(12) United States Patent
Ouchi

(10) Patent No.: US 6,503,192 B1
(45) Date of Patent: Jan. 7, 2003

(54) INSERTION FACILITATING DEVICE FOR INTESTINAL ENDOSCOPE

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/572,584

(22) Filed: May 17, 2000

(30) Foreign Application Priority Data

May 18, 1999 (JP) ............................................. 11-137298

(51) Int. Cl.$^7$ ................................................. A61B 1/04
(52) U.S. Cl. ........................ 600/114; 600/128; 600/135; 600/115
(58) Field of Search ................................. 600/114, 115, 600/128, 135, 200, 105

(56) References Cited

U.S. PATENT DOCUMENTS

| | | | | |
|---|---|---|---|---|
| 3,805,770 A | * | 4/1974 | Okada ......................... | 600/114 |
| 3,815,646 A | * | 6/1974 | Coakley ..................... | 141/337 |
| 3,866,601 A | * | 2/1975 | Russell ....................... | 600/114 |
| 4,167,939 A | * | 9/1979 | Storz ............................. | 128/4 |
| 4,332,242 A | * | 6/1982 | Chikama ............... | 128/200.26 |
| 4,538,594 A | * | 9/1985 | Boebel et al. .............. | 600/102 |
| 4,901,776 A | * | 2/1990 | Attinello .................... | 116/228 |
| 5,337,733 A | * | 8/1994 | Bauerfeind et al. ......... | 600/114 |
| 5,569,159 A | * | 10/1996 | Anderson et al. ........... | 600/114 |
| 5,688,224 A | * | 11/1997 | Forkey et al. ............... | 600/129 |
| 5,779,624 A | * | 7/1998 | Chang ......................... | 600/114 |
| 5,916,150 A | * | 6/1999 | Sillman ...................... | 600/184 |
| 5,993,379 A | | 11/1999 | Ouchi et al. | |
| 6,315,713 B1 | * | 11/2001 | Takada ....................... | 600/114 |

FOREIGN PATENT DOCUMENTS

| | | |
|---|---|---|
| JP | 59-31207 | 9/1984 |
| JP | 61276531 | 12/1986 |
| JP | 4-6723 | 2/1992 |
| JP | 4-18563 | 4/1992 |
| JP | 4-23523 | 6/1992 |
| JP | 5-35101 | 5/1993 |
| JP | 3030285 | 8/1996 |
| JP | 8-243075 | 9/1996 |
| JP | 10225430 | 5/1998 |
| JP | 10225430 | 8/1998 |

* cited by examiner

*Primary Examiner*—Linda C. M. Dvorak
*Assistant Examiner*—Jocelyn Ram
(74) *Attorney, Agent, or Firm*—Greenblum & Bernstein, P.L.C.

(57) ABSTRACT

An insertion facilitating device for an intestinal endoscope has a cylindrical body in which an insertion portion of an endoscope for a large intestine is inserted while holding an anal sphincter of a patient in an open position. The cylindrical body is provided at one end thereof with a conical opening.

10 Claims, 6 Drawing Sheets

INSERTION FACILITATING DEVICE FOR INTESTINAL ENDOSCOPE

BACKGROUND OF THE INVENTION

1. Field of the Invention

The present invention relates to an insertion facilitating device which is adapted to facilitate an insertion or removal of an endoscope, into or from a body cavity, for examination of a large intestine.

2. Description of the Prior Art

When an intestinal endoscope is inserted into a body cavity of a patient from the anus, the insertion portion of the endoscope (flexible tube) is pressed by the anal sphincter, so that it is difficult for the flexible tube to move. If the flexible tube is forcedly moved, the anal sphincter tends to strongly compress the flexible tube due to pain, so that it becomes more difficult to move the flexible tube.

To ease the patient's pain upon insertion of the endoscope and to facilitate the insertion operation, a xylocain jelly or the like is manually applied by an operator to the surface of the flexible tube for topical anesthesia and lubrication, so that the flexible tube can be smoothly moved into the anus. However, since the length of the longest flexible tube of the intestinal endoscope is 1.7 m, the lubricant tends to be exhausted in a short time in accordance with the movement of the flexible tube. Since a shortage of the lubricant causes the anal sphincter to be drawn by the flexible tube, it is necessary to frequently apply the lubricant to the flexible tube. Moreover, the operator's hand tends to slip due to the lubricant when the operator inserts the flexible tube while holding the same by his or her hand. The lubricant sticking to the operator's hand tends to dirty the endoscope or the surroundings, and the lubricant dripping from the endoscope dirties or contaminates the patient's bed.

Japanese Examined Utility Model Publication No. 4-6723 or No. 4-18563 show, by way of example, a sliding tube which makes it possible to easily insert the flexible tube in an inner portion of the large intestine by maintaining the intestine straight or linear. However, the sliding tube has drawbacks; namely, that mucous membrane gets caught in the space defined between the sliding tube and the flexible tube within the body cavity, and that the attachment or detachment of the sliding tube cannot be easily carried out. Under these circumstances, measures to insert the flexible tube in an inner portion of the large intestine without using the sliding tube have been proposed.

SUMMARY OF THE INVENTION

It is an object of the present invention to facilitate insertion and movement of an intestinal endoscope in a large intestine by holding the anal sphincter in an open position.

To achieve the object, according to the present invention, there is provided an insertion facilitating device for an intestinal endoscope, having a cylindrical body in which an insertion portion of an endoscope for a large intestine is inserted while holding an anal sphincter of a patient in an open position, wherein said cylindrical body is provided at one end thereof with a conical opening.

The length of said cylindrical body is preferably in the range of 30 mm to 150 mm, in view of the length of the anal sphincter and the rectum. If the maximum diameter of the conical opening is 2 to 5 times the outer diameter of the cylindrical body, it is possible to prevent the entirety of the insertion facilitating device from being inserted in a body cavity of a patient by mistake.

The insertion facilitating device can include a pressure leakage prevention member which is brought into elastic contact with the outer peripheral surface of the insertion portion of the inserted endoscope to prevent internal gas of the patient body from leaking out of the patient body. Substances discharged from the patient body can be discharged through a discharge port formed on the wall surface of the cylindrical body and can be collected in a reservoir. If at least one of the cylindrical body and the opening is provided with a through hole in which a moisture absorbing member is held, an operator can immediately remove or wipe a filth off with the moisture absorbing member. Consequently, a scattering of the filth can be prevented, thus resulting in a cleaner environment when the endoscope is being used. The cylindrical body can be provided with a large outer diameter portion and a small outer diameter portion arranged in this order from the insertion distal end of the cylindrical body. Consequently, the small outer diameter portion is pressed and held by the anal sphincter, so that the insertion facilitating device can be prevented from being accidentally slipped of f from the patient's anus.

The present disclosure relates to subject matter contained in Japanese Patent Application No. 11-137298 (filed on May 18, 1999) which is expressly incorporated herein by reference in its entirety.

BRIEF DESCRIPTION OF THE DRAWINGS

The invention will be discussed below in detail with reference to the accompanying drawings, in which.

DESCRIPTION OF THE PREFERRED EMBODIMENT

Figure 1:
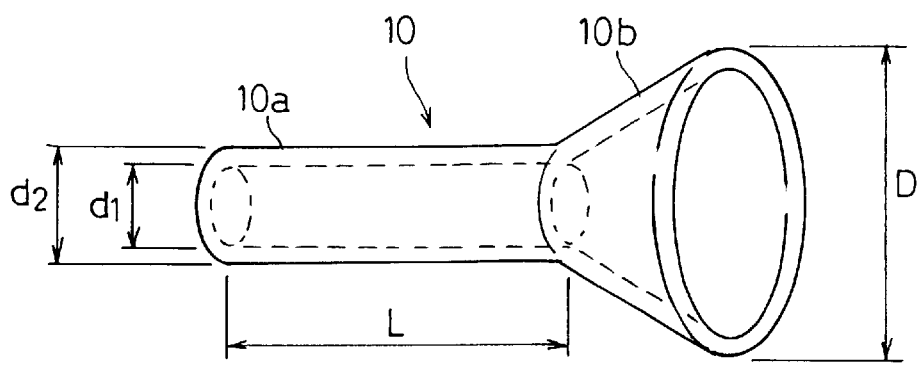
FIG. 1 is a perspective view of an insertion facilitating device for an intestinal endoscope according to a first embodiment of the present invention.
Figure 2:
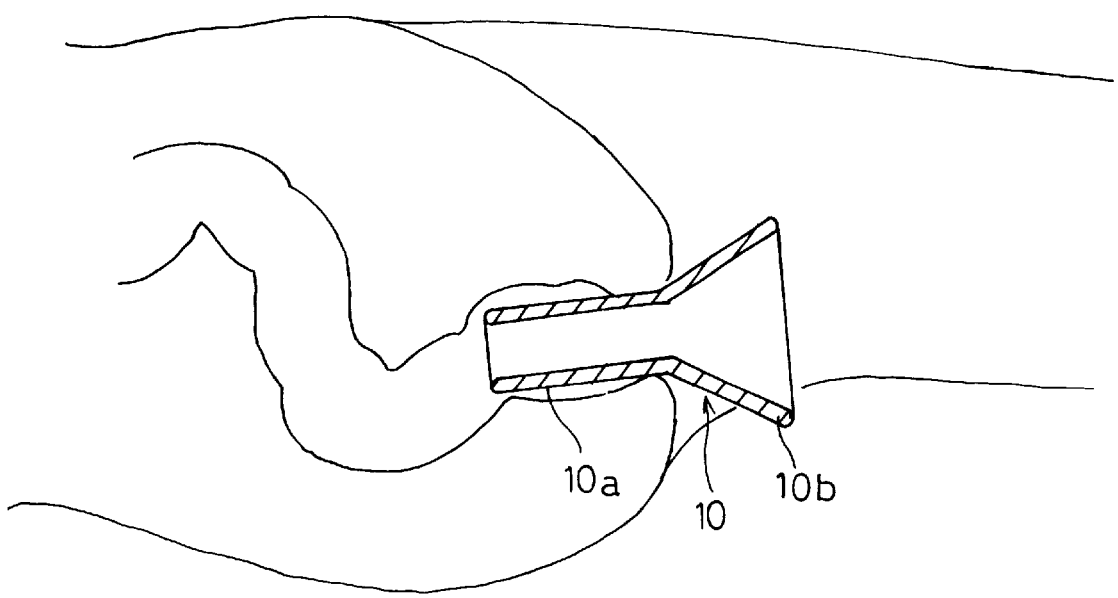
FIG. 2 is a schematic view of an insertion facilitating device for an intestinal endoscope, according to a first embodiment of the present invention, inserted into the anus of a patient.
Figure 3:
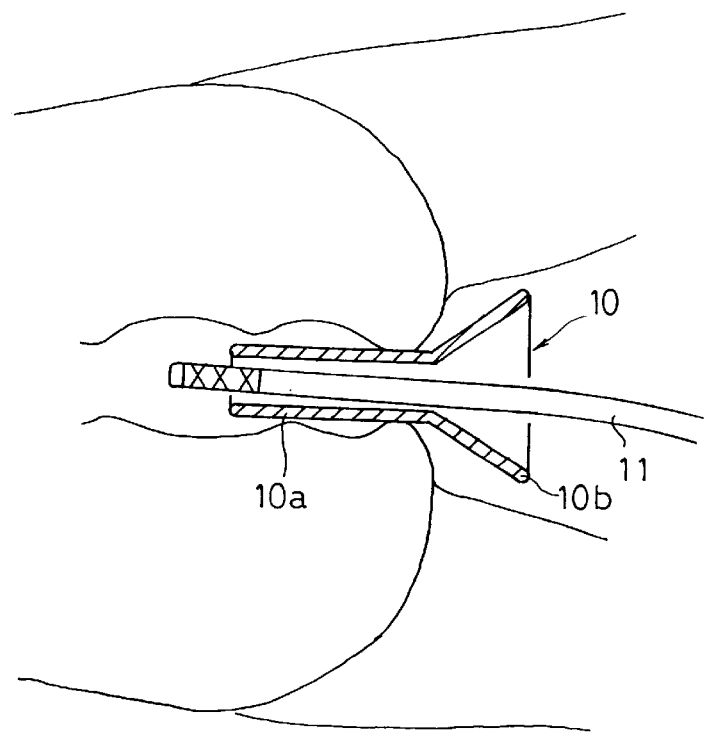
FIG. 3 is a schematic view of an insertion facilitating device for an intestinal endoscope, according to a first embodiment of the present invention, inserted into the anus of a patient, with the intestinal endoscope being inserted in a body cavity.

FIGS. 1 through 3 show a first embodiment of the present invention. As shown in FIG. 1, the insertion facilitating device 10 for a large intestine endoscope is composed of a cylindrical body 10a which is provided on one end thereof with a conical opening 110b. The inner diameter d1 of the cylindrical body 110a is such that an insertion portion (flexible tube) 11 of an intestinal endoscope (for a large intestine) can be easily inserted in the cylindrical body 10a. The outer diameter d2 of the cylindrical body 10a is preferably in the range of 10 to 20 mm, but can be larger, for example, 40 mm. The length L of the cylindrical body 10a is not smaller than 30 mm to hold the anal sphincter in an open position and is not greater than 150 mm in view of the length of the rectum. It is preferable that the maximum diameter D of the opening 10b is 2 to 5 times the outer diameter d2 of the cylindrical body 10a in order to facilitate the insertion of the flexible tube 11 into the opening 10b and to prevent the entire insertion facilitating device 10 from entering the body cavity of a patient by mistake. The insertion facilitating device 10 is preferably made of a material having a rigidity such that little deformation thereof due to contraction of the anal sphincter takes place so as to ensure a smooth movement of the flexible tube 11. Also, the material of which the insertion facilitating device 10 is made is preferably selected so that it does not injure the patient. Any materials which meet the requirements mentioned above can be used. For example, flexible synthetic resin can be used. If the insertion facilitating device 10 is made of Teflon (fluorocarbon resin) or is coated at its inner surface with Teflon to ensure a smooth sliding movement of the flexible tube 11, little lubricant is needed.

Upon examination using the intestinal endoscope, the cylindrical portion 10a of the insertion facilitating device 10 for a large intestine is inserted into a body cavity of a patient through the anus, with the opening 10b being located outside the patient body. Since the anal sphincter of the patient is kept in an open position by the cylindrical body 10a, the flexible tube 11 can be smoothly inserted without being obstructed by the anal sphincter. Furthermore, since the flexible tube 11 is not pressed by the anal sphincter, only one application of lubricant is needed.

Figure 4:
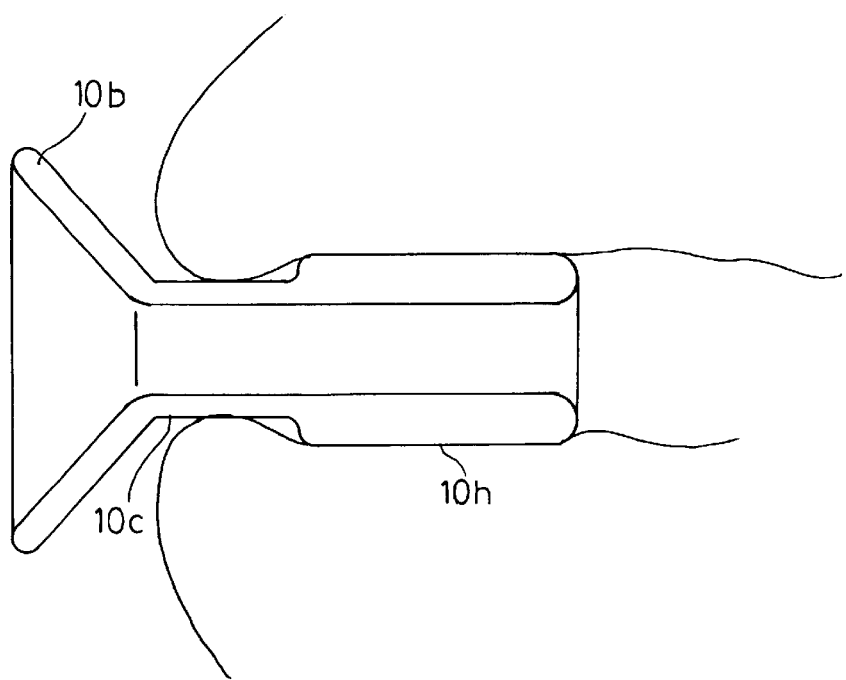
FIG. 4 is a schematic view of an insertion facilitating device for an intestinal endoscope, according to a second embodiment of the present invention, inserted into the anus of a patient, with the small diameter portion being squeezed by the anal sphincter.
Figure 5:
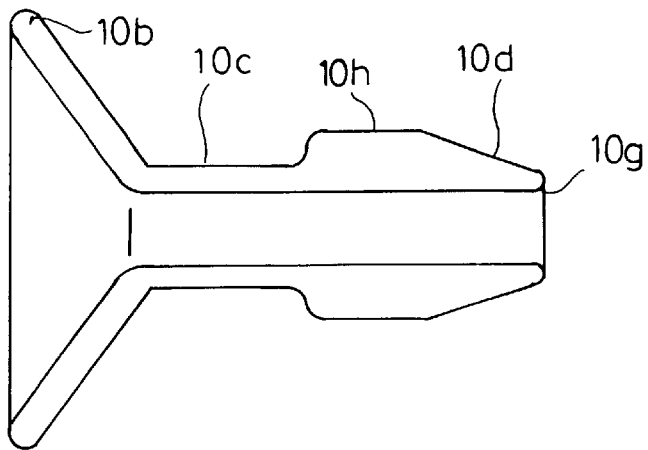
FIG. 5 shows a modification of an insertion facilitating device for an intestinal endoscope according to a second embodiment of the present invention.

FIG. 4 shows a second embodiment of an insertion facilitating device 10 for an intestinal endoscope according to the present invention. In the second embodiment, the cylindrical body 10a is provided with a small outer diameter portion 10c in the vicinity of the end opening 10b, so that the insertion facilitating device 10 can be prevented from slipping out of the anus. Since the outer small diameter portion 10c is pressed and firmly held by the anal sphincter, the insertion facilitating device 10 can be stably held in the anus during the insertion or removal of the flexible tube 11 in or from the insertion facilitating device. Moreover, as shown in FIG. 5, it is possible to provide a tapered portion 10d whose diameter is gradually reduced toward the distal end 10g of the cylindrical body 10a that is to be inserted in the patient's body, so that the insertion of the insertion facilitating device 10 into the patient's anus can be facilitated due to the tapered end (conical end) 10d.

Figure 6:
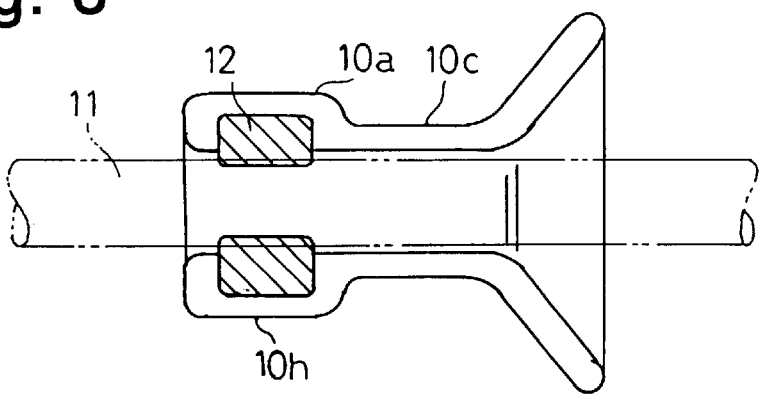
FIG. 6 is a sectional view of an insertion facilitating device for an intestinal endoscope according to a third embodiment of the present invention.
Figure 7:
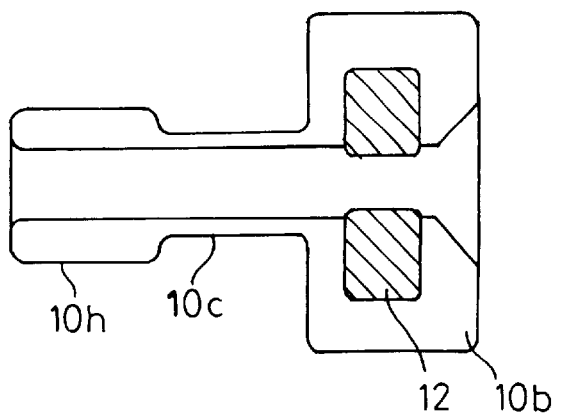
FIG. 7 shows a modification of an insertion facilitating device for an intestinal endoscope according to a third embodiment of the present invention.

FIG. 6 shows a third embodiment of the present invention, in which the cylindrical body 10a is provided on its inner surface with a pressure leakage prevention ring 12 made of a sponge material. The inner diameter of the pressure leakage prevention ring 12 is smaller in a free state than the outer diameter of the flexible tube 11, so that the inside of the patient's body (anus) is isolated from the outside of the patient's body by the pressure leakage prevention ring 12 when the flexible tube 11 is inserted in the anus, thus resulting in no leakage of internal air of the patient's body. Preferably, the thickness and hardness of the pressure leakage prevention ring 12 are selected so as to resist a pressure of approximately 0.1 Pa, so that if the internal pressure becomes excessively high, the internal gas can be discharged outside to prevent the insertion facilitating device 10 from being damaged or broken. Alternatively, it is possible to provide the pressure leakage prevention ring 12 at the opening 10b, as shown in FIG. 7.

Figure 8:
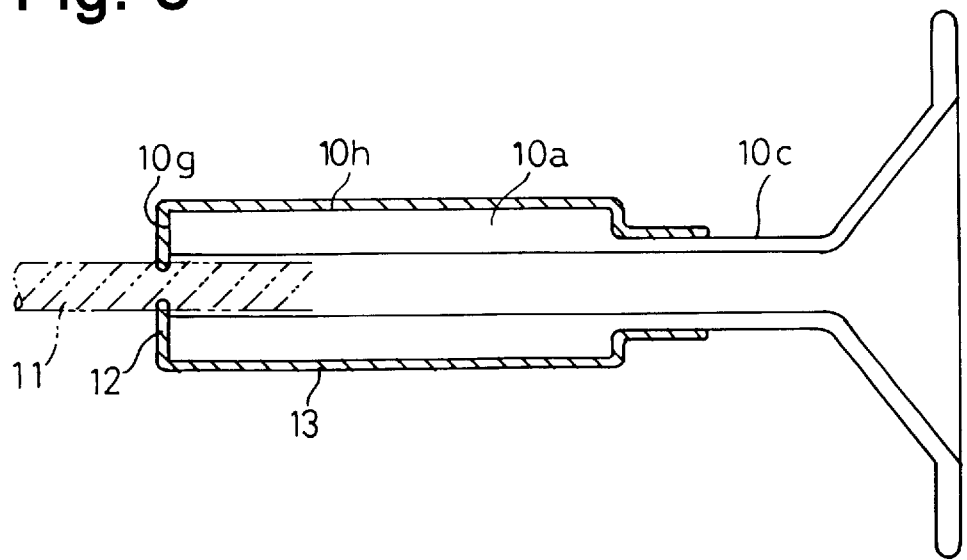
FIG. 8 is a sectional view of an insertion facilitating device for an intestinal endoscope according to a fourth embodiment of the present invention.
Figure 9:
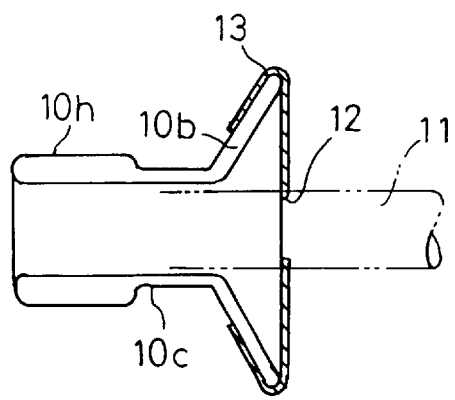
FIG. 9 is a sectional view of an insertion facilitating device for an intestinal endoscope according to a fourth embodiment of the present invention.

FIGS. 8 and 9 show a fourth embodiment of the present invention. In FIG. 8, the pressure leakage prevention ring 12 in the third embodiment is provided on a rubber cover 13 which covers the cylindrical body 10a. The rubber cover 13 extends from the small diameter portion 10c of the cylindrical body 10a to the insertion end 10g thereof. The pressure leakage prevention ring 12 is formed on the insertion end log. In a modification shown in FIG. 9, the cover 13 covers the opening 10b and the pressure leakage prevention ring 12 is formed with the opening 10b.

Figure 10:
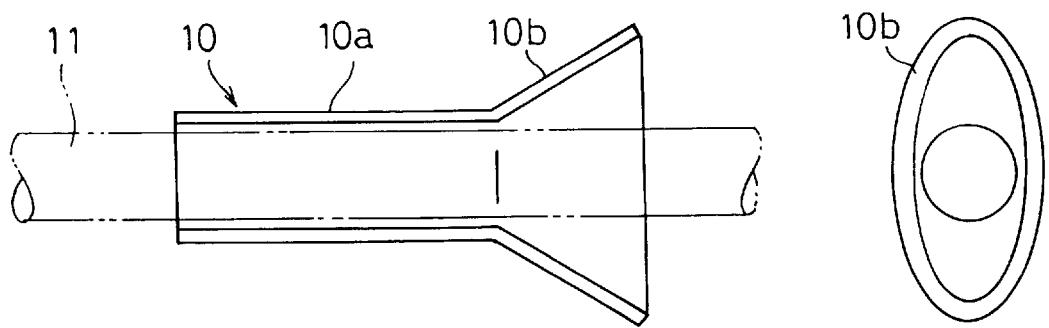
FIG. 10 is a sectional view of an insertion facilitating device for an intestinal endoscope according to a fifth embodiment of the present invention.

FIG. 10 shows a fifth embodiment of the present invention. In the fifth embodiment, the opening 10b is elliptical, so that it can be held in the patient's buttocks and thus the insertion facilitating device 10 can be stably attached to the patient.

Figure 11:
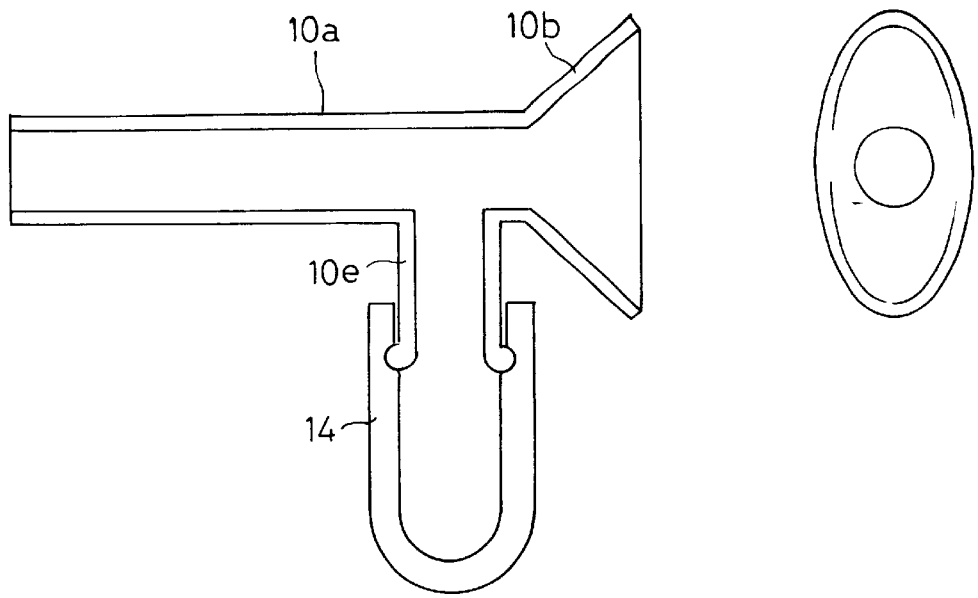
FIG. 11 is a sectional view of an insertion facilitating device for an intestinal endoscope according to a sixth embodiment of the present invention.
Figure 12:
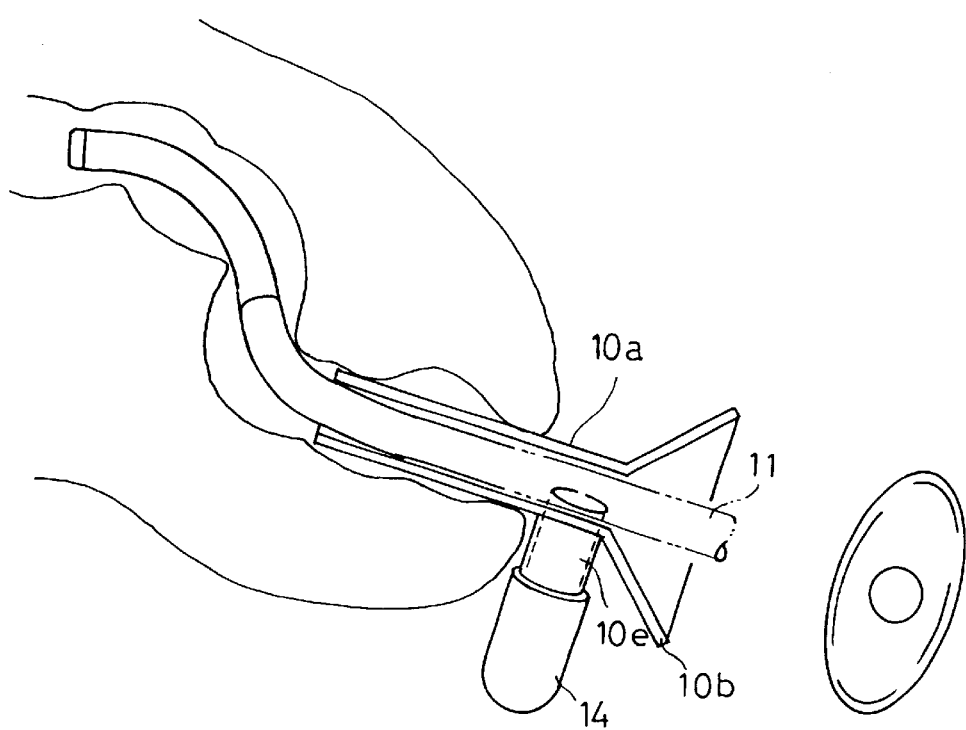
FIG. 12 is a sectional view of an insertion facilitating device for an intestinal endoscope, according to a sixth embodiment of the present invention, with an endoscope being inserted therein.

FIGS. 11 and 12 show a sixth embodiment of the present invention. In FIG. 11, the cylindrical body 10a is provided on the wall surface thereof with a discharge port 10e through which filth, such as mucus or washing liquid for the intestines can be discharged out of the patient body. Preferably, a detachable reservoir 14 is attached to the discharge port 10e, so that the filth can be collected therein. In FIG. 12, the insertion facilitating device 10 is inserted in the patient's anus and the flexible tube 11 is inserted into the patient body through the insertion facilitating device 10. Since the filth discharged from the patient body is collected in the reservoir 14, no filth drips, or is discharged from, the opening 10b, thus resulting in no contamination of the surroundings by the filth.

Figure 13:
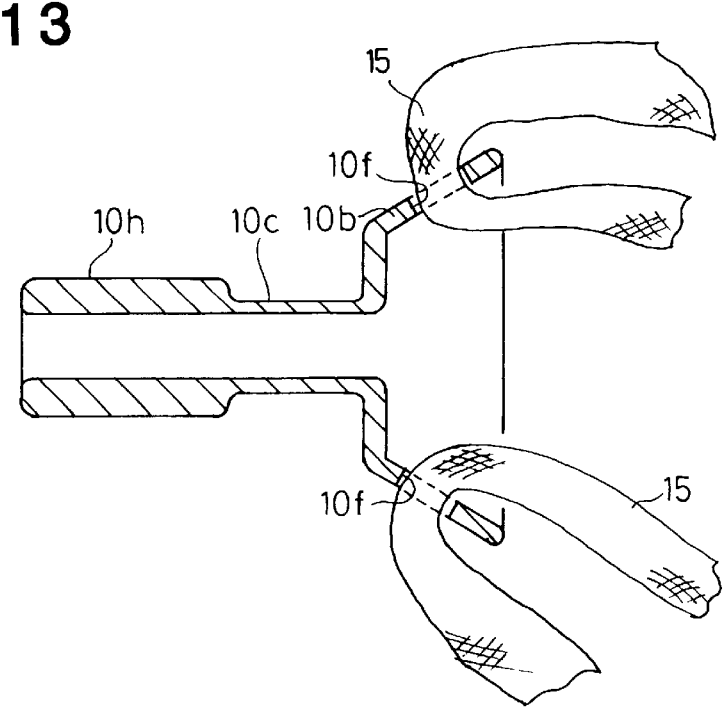
FIG. 13 is a sectional view of an insertion facilitating device for an intestinal endoscope according to a seventh embodiment of the present invention.
Figure 14:
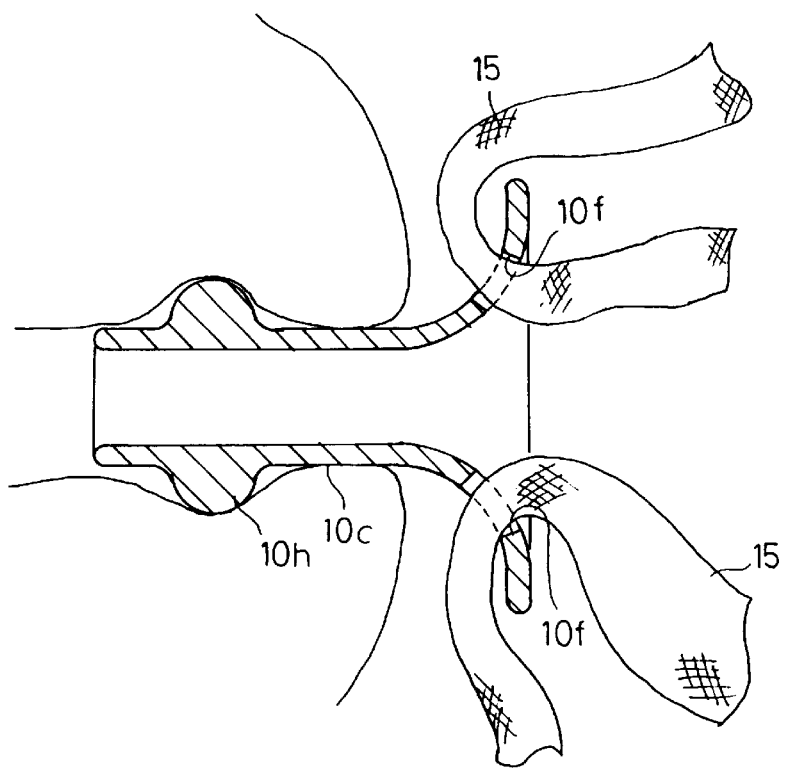
FIG. 14 is a sectional view of an insertion facilitating device for an intestinal endoscope according to an eighth embodiment of the present invention.

Seventh and eighth embodiments of the present invention are shown in FIGS. 13 and 14, respectively. In the seventh embodiment shown in FIG. 13, through holes 10f are formed in the wall of the opening 10b of the insertion facilitating device 10 having the small diameter portion 10c similar to the second embodiment. Hygroscopic members (moisture absorbing member) 15 having a water absorbing capability are inserted and held in the through holes 10f. With this arrangement, the operator can immediately wipe his or her hand dirtied during the operation of the flexible tube 11, on the gauze 15. Furthermore, if the peripheries of the patient's anus are covered by the gauzes 15, it is possible to prevent the filth from being scattered.

In the eighth embodiment shown in FIG. 14, the cylindrical body 10a is provided with an annular projection 10h (large outer diameter portion) which prevents the insertion facilitating device 10 from being slipped off from the anus. The through holes 10f are formed at the opening 10b of the insertion facilitating device 10. Alternatively, it is possible to form the through holes 10f on the wall portion of the cylindrical body 10a other than the opening 10b. It is also possible to hold the gauzes 15 on the insertion facilitating device 10, by means of clips or the like.

As can be understood from the above discussion, according to the present invention, since the flexible tube is not pressed or squeezed by the anal sphincter of the patient, the flexible tube can be smoothly and easily inserted or removed, thus leading to a reduction in the time for inspection using the endoscope. Moreover, since the anus is not drawn or rubbed by the flexible tube, the patient's pain upon inspection using the endoscope is eased. Furthermore, since a large amount of lubricant is unnecessary, the endoscope can be used in a cleaner environment.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An insertion facilitating device for an intestinal endoscope, comprising:
   a cylindrical body for holding an anal sphincter of a patient in an open position and having a length within a range of 30 mm to 150 mm, an insertion portion of the intestinal endoscope being insertable through the cylindrical body; and
   a conical opening portion, positioned at one end of the cylindrical body, having a maximum diameter within a range of 2 to 5 times an outer diameter of the cylindrical body; and
   a pressure leakage preventer, positioned in the cylindrical body, for preventing internal gas of the patient from escaping, the pressure leakage preventer being elastically contactable with an outer peripheral surface of the insertion portion of the intestinal endoscope.

2. The insertion facilitating device for an intestinal endoscope, according to claim 1, further comprising;
   a discharge port, positioned on a wall surface of the cylindrical body, that enables substances from the patient to be discharged from the cylindrical body; and
   a reservoir that collects the substances discharged through the discharge port.

3. The insertion facilitating device for an intestinal endoscope, according to claim 1, at least one of the cylindrical body and the conical opening portion defining a through hole for holding a moisture absorbing member.

4. The insertion facilitating device for an intestinal endoscope, according to claim 1, the cylindrical body comprising a first outer diameter portion, located adjacent to a distal end of the cylindrical body insertable in the patient's sphincter, and a second outer diameter portion, located in an intermediate portion of the cylindrical body, the first outer diameter portion being larger than the second outer diameter portion.

5. An insertion facilitating device for an intestinal endoscope, comprising:
   a cylindrical body for holding an anal sphincter of a patient in an open position and having a length within a range of 30 mm to 150 mm, an insertion portion of the intestinal endoscope being insertable through the cylindrical body;
   a conical opening portion, positioned at one end of the cylindrical body, having a maximum diameter within a range of 2 to 5 times an outer diameter of the cylindrical body;
   a discharge port, positioned on a wall surface of the cylindrical body, for enabling substances from the patient to be discharged from the cylindrical body; and
   a reservoir for collecting the substances discharged through the discharge port.

6. The insertion facilitating device, according to claim 5, at least one of the cylindrical body and the conical opening portion defining a through hole for holding a moisture absorbing member.

7. The insertion facilitating device, according to claim 5, the cylindrical body comprising a first outer diameter portion, located adjacent to a distal end of the cylindrical body insertable in the patient's sphincter, and a second outer diameter portion, located in an intermediate portion of the cylindrical body, the first outer diameter portion being larger than the second outer diameter portion.

8. An insertion facilitating device for an intestinal endoscope, comprising:
   a cylindrical body for holding an anal sphincter of a patient in an open position and having a length within a range of 30 mm to 150 mm, an insertion portion of the intestinal endoscope being insertable through the cylindrical body; and
   a conical opening portion, positioned at one end of the cylindrical body, having a maximum diameter within a range of 2 to 5 times an outer diameter of the cylindrical body;
   at least one of the cylindrical body and the conical opening portion defining a through hole for holding a moisture absorbing member.

9. The insertion facilitating device, according to claim 8, the cylindrical body comprising a first outer diameter portion, located adjacent to a distal end of the cylindrical body insertable in the patient's sphincter, and a second outer diameter portion, located in an intermediate portion of the cylindrical body, the first outer diameter portion being larger than the second outer diameter portion.

10. An insertion facilitating device for an intestinal endoscope, comprising:
    a cylindrical body for holding an anal sphincter of a patient in an open position, an insertion portion of the intestinal endoscope being insertable through the cylindrical body, the cylindrical body comprising a first outer diameter portion, located adjacent to a distal end of the cylindrical body insertable in the patient's sphincter, and a second outer diameter portion, located in an intermediate portion of the cylindrical body, the first outer diameter portion being larger than the second outer diameter portion; and
    a conical opening portion, positioned at one end of the cylindrical body, having a maximum diameter within a range of 2 to 5 times an outer diameter of the cylindrical body.

* * * * *